(12) United States Patent
Engels et al.

(10) Patent No.: US 8,025,992 B2
(45) Date of Patent: Sep. 27, 2011

(54) BLOCK AND METHOD OF MAKING

(75) Inventors: Alexander Engels, Feldkirch (AT); Alfred Hämmerle, Koblach (AT)

(73) Assignee: Ivoclar Vivadent AG, Schaan (LI)

( * ) Notice: Subject to any disclaimer, the term of this patent is extended or adjusted under 35 U.S.C. 154(b) by 1167 days.

(21) Appl. No.: 11/804,202

(22) Filed: May 17, 2007

(65) Prior Publication Data

US 2007/0272120 A1    Nov. 29, 2007

(30) Foreign Application Priority Data

May 23, 2006  (DE) .......................... 10 2006 024 065
Mar. 8, 2007  (DE) .......................... 10 2007 011 339

(51) Int. Cl.
*B32B 9/00* (2006.01)

(52) U.S. Cl. ........................ 428/701; 428/702

(58) Field of Classification Search ........................ None
See application file for complete search history.

(56) References Cited

U.S. PATENT DOCUMENTS

| | | |
|---|---|---|
| 4,751,099 A | 6/1988 | Niino et al. |
| 5,263,858 A | 11/1993 | Yoshida et al. |
| 5,455,000 A | 10/1995 | Seyferth et al. |
| 5,656,564 A | 8/1997 | Nakayama et al. |
| 6,171,572 B1 | 1/2001 | Aozasa |
| 6,379,593 B1 | 4/2002 | Datzmann et al. |
| 6,713,421 B1 | 3/2004 | Hauptmann et al. |
| 2002/0136658 A1 | 9/2002 | Dilmore et al. |

FOREIGN PATENT DOCUMENTS

| | | |
|---|---|---|
| DE | 199 44 130 A1 | 4/2001 |
| EP | 0 255 954 A2 | 2/1988 |
| EP | 1 076 036 A1 | 2/2001 |
| WO | WO 02/09612 A1 | 2/2002 |

*Primary Examiner* — Timothy Speer
(74) *Attorney, Agent, or Firm* — Ann M. Knab

(57) ABSTRACT

The invention relates to a block (10) made of ceramic compounds, in particular dental compounds, of at least one ceramic compound (15) with predetermined first optical properties and at least a second ceramic compound (17) with predetermined second optical properties, and of a transition area between the two ceramic compounds, which transition area is composed of changing mixtures of the at least two ceramic compounds, the variation gradient of the mixtures being substantially constant. The invention further relating to a process for making such a block.

20 Claims, 2 Drawing Sheets

BLOCK AND METHOD OF MAKING

CROSS-REFERENCE TO RELATED APPLICATIONS

This application claims foreign priority benefits under 35 U.S.C. §119 from German patent application Ser. No. 10 2006 024 065.0 filed May 23, 2006, and from German patent application Ser. No. 10 2006 011 339.2 filed Mar. 8, 2007.

TECHNICAL FIELD

The invention relates to a block made of ceramic compounds, in particular dental compounds, and more particularly to a block made of at least one ceramic compound with predetermined first optical properties and at least a second ceramic compound with predetermined second optical properties, and of a transition area between the two ceramic compounds, which transition area is composed of changing mixtures of the at least two ceramic compounds, the variation gradient of the mixtures being substantially constant.

BACKGROUND OF THE INVENTION

To produce teeth, tooth parts or dental restorations (hereinafter referred to as tooth), blocks are generally prefabricated and are presintered, for example at a temperature of approximately 900° C. to 1100° C. In this state, the block thus produced can be easily machined, for example by milling. The milling work results in the formation of a shaped article which thereafter simply has to undergo final sintering in order to achieve the required dimension and final hardness. When producing the shaped article, account has to be taken of the shrinkage that occurs in dense sintering. The shrinkage and the strength always derive from the sintering conditions (especially temperature, time, atmosphere) under which the block is produced.

To ensure that the restorations appear as true to nature as possible, it has already been proposed to combine different layers, each differently colored, of ceramic compounds in order to form a tooth. For example, according to this proposal, up to 10 very thin layers of ceramic compounds can be presintered together, such that a shaped article with a suitable color profile can be obtained. If the differently colored layers each have different chemical characteristics, however, there is a danger of the presintering temperature also being different. The compound sintering at higher temperatures then melts on the particle boundaries less strongly than the compound sintering at lower temperatures. This can result in different shrinkages and bond strengths, which make the final production more problematic.

Such block bodies can be made, for example, from ceramics based on $ZrO_2$. However, it is also quite possible to use glasses and also glass ceramics as the starting material. In glass ceramics, primary particles are typically generated from glass granules by comminution, their particle size lying in the range from 0.5 to 50 micrometers. In the context of this invention, particle size and the corresponding indicated sizes are always understood as the $d_{50}$ value, which corresponds to the diameter at 50% on the frequency distribution curve of particles, as measured according to ISO 13320. Coloring is usually effected by addition of coloring oxides to the melt from which the granulate is obtained, or to the ground granulate. These oxides are then present separately.

To make available an improved block, it has also been proposed to match the color profile to the color profile of an existing tooth. A natural tooth typically has a bright or whitish incisal area and a more strongly colored cervical area. Extending between these areas there is the central area within which the color changes. Between the cervical area and the central area, on the one hand, and between the central area and the incisal area, on the other hand, the color transition weakens, with the result that the variation gradient is typically configured in the manner of a flat Gaussian curve. However, the attempts to simulate a suitable color profile by corresponding layering of ceramic compounds surprisingly led to aesthetically unsatisfactory results, which were also difficult to produce.

OBJECTS AND SUMMARY OF THE INVENTION

The object of the invention is to make available an aesthetically much improved block made of ceramic compounds, in particular for the dental sector.

Surprisingly, the block according to the invention, with the substantially constant variation gradient, provides an optically "lighter" look to the tooth. The translucency in the incisal area is particularly noticeable, without giving the hitherto typical impression of an artificial tooth, not even upon closer inspection.

The variation gradient tailored closely to the required optical properties requires the mixing ratio, as viewed from the incisal area, to initially increase slightly less strongly to the dark color than would be the case with a linearly changing mixing ratio. The reason for this is that a chrominance is more strongly perceived by the human eye and accordingly makes a stronger visual impression than a simple difference in brightness. According to the invention, it is particularly expedient that the constancy of the variation gradient is not limited to fixing the variation gradient for example of the brightness or chrominance. It is instead expedient if the resulting variation gradient is constant. For example, as viewed from the incisal area again, the chrominance can initially be markedly changed and the brightness can be changed to a lesser extent, and accordingly, at a later stage, that is to say when approaching the cervical area, the chrominance can change less markedly and the brightness more markedly.

According to the invention, it is also particularly expedient that a gradual change of the physical parameters in the transition area between the first ceramic compound and the second ceramic compound minimizes stresses. If both ceramic compounds have different degrees of shrinkage and/or bond strengths, for example, the stresses thus generated in the block are distributed over a greater area, with the result that local stress peaks are minimized.

The provision of a transition area with a substantially constant variation gradient of the optical properties does not rule out the possibility that in another area, for example adjacent thereto, the optical properties can be substantially constant. This concerns, for example, the outermost incisal area, or the outermost cervical area, which is generally covered by gum in the patient's mouth, such that no esthetic measures have to be taken here.

It should also be noted that, in incisors, the material strength usually decreases sharply toward the incisal area. For this reason too, the translucency increases toward the incisal area, with the result that an area with constant optical properties can be provided there.

In a solution of this kind, it is expedient, between the transition area with the constant variation gradient and the areas with constant optical properties, to provide in each case additional crossover areas in which the variation gradient changes.

According to the invention, it is particularly expedient that the block according to the invention has a transition area that extends across almost its full height. The height is preferably greater than the height of a human tooth, thus affording the possibility of shifting the coloration of the tooth in the direction of one color or in the direction of the other color, without losing the inventive effect of harmonious color transition.

In another preferred embodiment, the color transition is not level, but slightly curved, preferably such that the darker color extends farther down in the center and the brighter color, which is typically to be assigned to the incisal area, extends further up on the outside. Down and up relate here to the position of a block from which a tooth is to be milled for the upper jaw. By means of the curved configuration of the color transition planes, the natural tooth appearance can be simulated in greater detail, since in the natural tooth too the dentine is typically surrounded by enamel.

According to the invention, the variation gradient of the resulting optical properties of the transition area is substantially constant. It will be noted that such constancy (in the range of measurement accuracy) is sought, and a deviation of 2, 5 or even 10%, for example, is still defined as constant.

In another modified embodiment, the aim is to keep the variation gradient of the resulting physical properties substantially constant. The aforementioned definition of constancy basically applies in this case too. Such physical properties can include strength, for example, although this is possible only if similar ceramic compounds are used, for example either two glass ceramics or two oxide ceramics. It will be appreciated that, in this embodiment, a prerequisite is the use of ceramics with at least substantially similar sintering conditions.

For producing the block according to the invention using zirconium dioxide ceramics, the ceramics are preferably metered in granulate form. The granulates are broken up by pressing, and particles measuring from 0.1 to approximately 1 micrometer can be formed from a granulate size of preferably 50 to 400 micrometers.

By contrast, when using glass ceramics, the glass granulate can be present with a particle size that corresponds to the primary particles, for example in the range of 1 to 25 micrometers.

In this connection, it may be expedient to initially work this powder up into a flowable granulate.

Although provision is made, according to the invention, to control the mixing ratio on the basis of the resulting properties of two ceramic compounds, the invention does not exclude the possibility of combining these with a third ceramic compound or even with still more ceramic compounds.

The invention is also described here mainly with reference to oxide ceramics, for example $ZrO_2$. However, this does not exclude applying the measures according to the invention to glasses, glass ceramics and other ceramics.

According to the invention, it is particularly expedient, in addition to the transition area with the non-zero variation gradient of the optical properties, to provide an area with substantially constant optical properties.

According to the invention, it is particularly expedient that, between the area with constant optical properties (=variation gradient equals zero) and the transition area with a substantially constant variation gradient, a crossover area is provided in which the gradient changes from zero to the non zero value of the variation gradient.

According to the invention, it is particularly expedient that the block has substantially a cuboid shape or tablet shape, with the length and width each being smaller than the height.

Alternatively, according to the invention, it is expedient that the block is present in a cuboid shape, with the length or width being greater than the height.

According to the invention, it is particularly expedient that the block has substantially a cuboid shape, the midpoint of its height being formed by the transition area.

According to the invention, it is particularly expedient that the block is formed from a granulate of which the particle size is greater than 10 micrometers and smaller than 2 millimeters, in particular between 50 and 250 micrometers. It is expedient if at least 95% by weight of the granulate has a $d_{50}$ particle size in the range from 0.1 micrometer to 2 millimeters, at least 90% by weight in the range from 1 micrometer to 700 micrometers, and at least 85% by weight in the range from 50 to 400 micrometers. This can be achieved, for example, by suitable screening methods known per se, in which case it may be useful, in the case of glass ceramics, to initially convert existing powders into granulates by means of granulation aids, binders, etc.

According to the invention, it is particularly expedient that the block is constructed from ceramic compounds whose primary particle size is smaller than 10 micrometers and in particular greater than 10 nanometers.

According to the invention, it is particularly expedient that the block is produced in a mold which is acted upon by at least one press ram, preferably by two press rams lying opposite one another, in order to generate substantially a cuboid shape or tablet shape. In addition to the (monoaxial) pressing of the block using one or two press rams, isostatic pressing can also be carried out.

According to the invention, it is particularly expedient that the block is produced from a metered layering of ceramic compounds whose transition area is composed of mixtures of the at least two ceramic compounds and set with such a gradient that the variation gradient of the resulting optical properties is substantially constant in the transition area.

According to the invention, it is particularly expedient that, in a transition area between the first ceramic compound and the second ceramic compound, the variation profile of the mixing ratio at an inner location of the block, in particular in the center, is different than at the edge of the block, relative to a sectional plane of the block parallel to its base.

According to the invention, it is particularly expedient that the locations of identical mixing ratio between the two ceramic compounds lie on a surface that differs from a plane, and that in particular is curved.

According to the invention, it is particularly expedient that the surface is substantially a cone surface, the cone angle of which is greater than zero, in particular more than 0.5°, and smaller than approximately 30°.

According to the invention, it is particularly expedient that, in a transition area between the first ceramic compound and the second ceramic compound, points with identical optical properties on the outside lie in a different plane than inside the block.

According to the invention, a receiving cavity is provided which receives the material to be formed into the block of this invention, the material to be formed into the block being metered into the cavity, the metering being changed during the filling of the receiving cavity, and the compounds having particular and/or different mechanical properties, and, during the filling of the receiving cavity, the metering of the ceramic compounds and/or their mixing ratio being changed and the compounds have in particular different optical and/or mechanical properties.

Further advantages, details and features of the invention will become clear from the following description of an illustrative embodiment, with reference being made to the drawings, in which:

DETAILED DESCRIPTION

Figure 1:
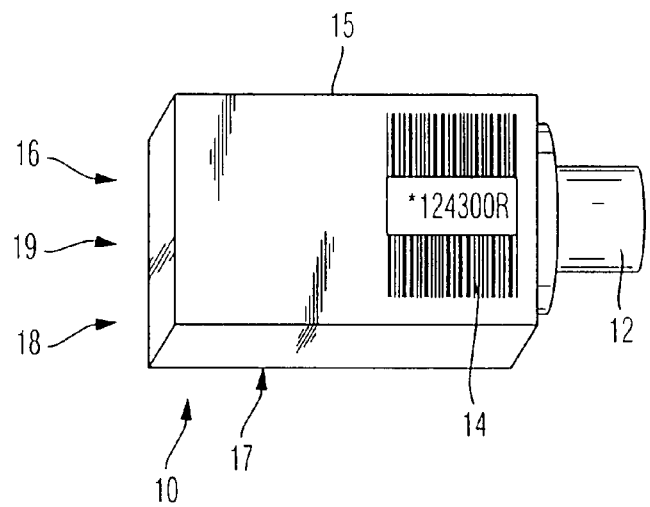
FIG. 1 shows a schematic, perspective side view of a block according to the invention.

The block 10 shown in FIG. 1 is composed of oxide ceramics, for example $ZrO_2$. In the embodiment shown, the block 10 consists of a first ceramic compound 15 and of a second ceramic compound 17, which are mixed in a particular way. It is produced by metered mixing of the ceramic compounds 15 and 17 from which it is made. After the metering, the block 10 is pressed and presintered in a manner known per se. In this state, it can be easily machined, for example milled, in order to remove material and produce a tooth as restoration part.

To simplify the machining, an extension piece 12 is mounted on the actual block 10 and is connected fixedly to the ceramic block 10. The block 10 can be clamped in the milling device via the extension piece 12.

In the view according to FIG. 1, the block 10 is shown in a position in which a darker tooth color is arranged at the top and a brighter tooth color is arranged at the bottom. This arrangement corresponds to a tooth in the upper jaw of a patient, since a tooth typically has a greater level of brightness and translucency in the incisal area 18 than in the cervical area 16.

According to the invention, a central area 19 extends between the cervical area 16 and the incisal area 18 and is configured in a particular way, as will be explained below with reference to the attached figures.

To achieve the best possible imitation of a natural appearance, starting from the cervical area 16 there is no direct gradation of the three areas, namely the cervical, central and incisal areas, but instead a gradual color change leading to the virtually or completely colorless incisal area 18 of the framework. The cervical area 16 colored with the one base color should take up at least 20% of the total height of the block 10. The gradual transition starts from there. Particularly preferably, the cervical area 16 takes up approximately 50% of the total height of the tooth.

Here, the direction from the cervical area 16 to the incisal area 18 is designated as the height of the tooth. In the illustrative embodiment shown, the block 10 according to the invention is cuboid, its width being considerably greater than its height, while its depth corresponds approximately to the height. This embodiment allows two substantially identical teeth to be produced from the block 10, the teeth each being produced from areas of the block 10 that lie next to one another in the plane of the drawing.

The height of the block 10 is considerably greater than the height of a tooth, for example by 50%. This allows the dental technician to adapt the position of the tooth in the block 10 in such a way as to satisfy the particular requirements, that is to say the dentition situation presented by the patient. If the position is chosen further down, a brighter tooth is automatically obtained, whereas, if the position is chosen further up, a darker tooth is automatically obtained.

It will be appreciated that the shape of the block 10 according to the invention is not limited to the cuboid shape. Instead of this, a tablet shape can be used, or a cuboid shape with a greater height than width, which is suitable for producing a single tooth.

Moreover, the degree of color change of the tooth can also be adjusted within wide ranges by setting the height of the block 10. With a greater height, for example corresponding to an overdimension of 100% relative to a tooth, the intensity of the color transition is less pronounced, whereas, with an overdimension of just 101, the color transition is more intense.

Figure 2:
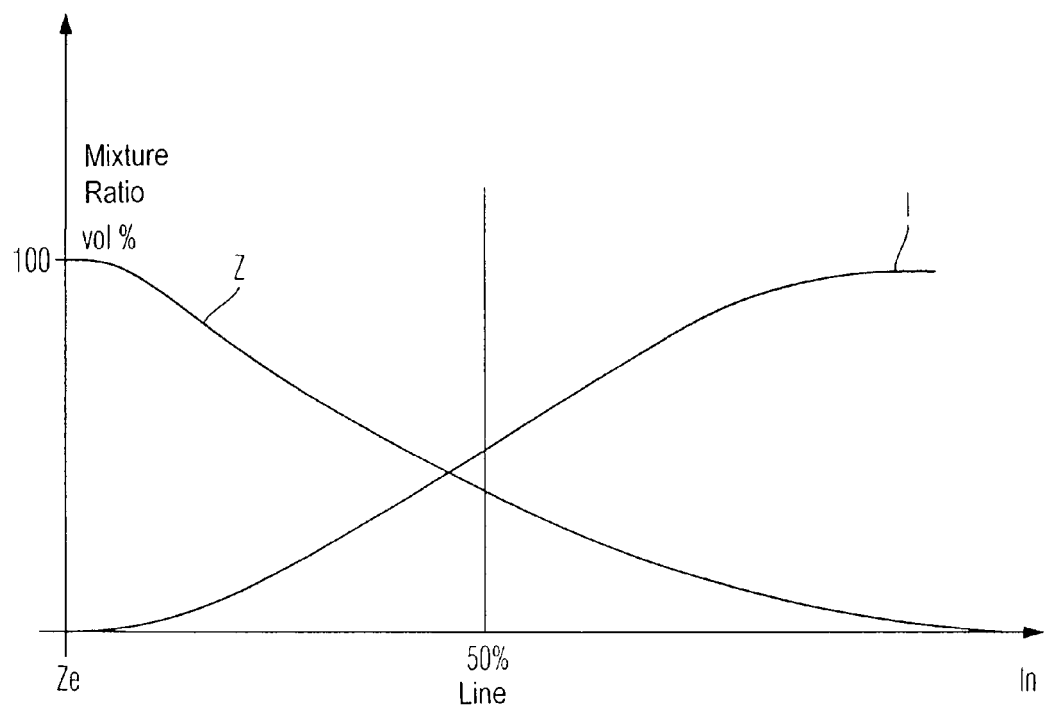
FIG. 2 shows a diagram illustrating the mixing ratio of the ceramic compounds, plotted over the height of the block, in the embodiment according to FIG. 1.

FIG. 2 shows a change in the mixing ratio of the ceramic compounds, plotted over the height of the block 10. In the cervical area 16 (at Ze), the cervical compound Z is present at almost 100%, whereas the incisal compound I is virtually absent or at the very most accounts for just a few percent.

By contrast, in the incisal area 18 (at In), the cervical compound Z is virtually absent, whereas the incisal compound I takes up a proportion of virtually 100%. Between these areas, the proportion of the cervical compound, as viewed from the direction of the cervical area 16, decreases continuously, whereas the proportion of the incisal compound increases continuously. In the illustrative embodiment shown, however, the proportion of the cervical compound decreases more strongly than linearly, and the proportion of the incisal compound accordingly increases more strongly than linearly, in each case viewed from the direction of the cervical area 16.

Figure 3:
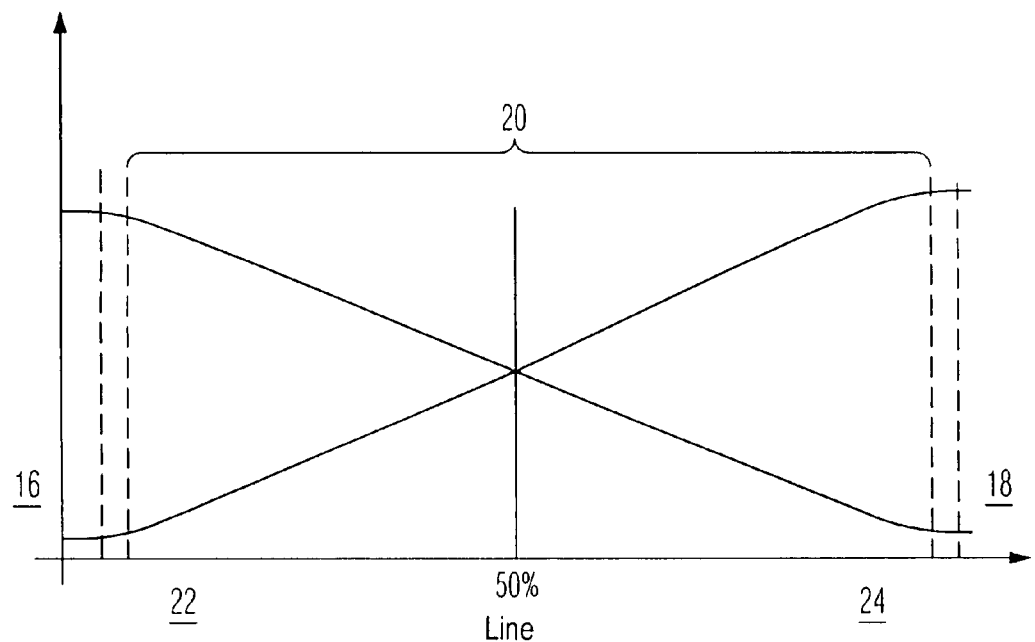
FIG. 3 shows a graph illustrating the optical 3 properties of the embodiment of the block according to FIG. 1.

The point of intersection of the two curves of the cervical compound and of the incisal compound is therefore reached before the center between cervical area 16 and incisal area 18. This is marked in FIG. 2 by the 50% line. The reason for this is, according to the invention, to achieve a constant variation gradient of the optical properties, as is shown in FIG. 3. It will be appreciated that, depending on the choice of the relevant optical properties, the offset of the 50% line relative to the geometric center can also take place in the other direction. The human eye perceives intense colors more strongly, which fact is compensated according to the invention, with the result that, if chrominance is chosen as the optical property, the appropriate distribution is obtained.

Figure 4:
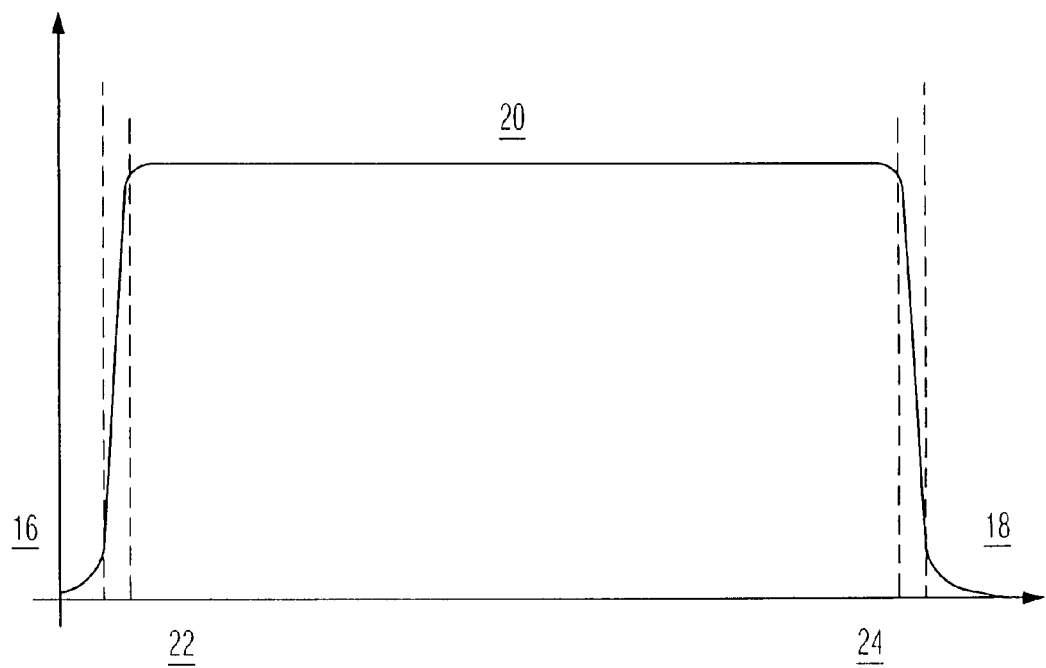
FIG. 4 shows the variation gradient of the optical properties in a graph, plotted over the height of the block according to FIG. 1.

FIG. 3 shows the profile of the optical properties over the height of the block. Between the cervical area 16 and the incisal]. area 18, the variation gradient of the optical properties, as can be seen from FIG. 4, is constant, such that the optical properties can each basically be plotted in a straight line with constant gradient. This area Is designated as transition area 20. For technical reasons, between the cervical area 16 and the transition area 20, and between the transition area 20 and the incisal area 18, there is in each case a crossover area 22, 24, respectively, in which the gradient of the curve increases or decreases to the constant value.

For the sake of simplicity, in the illustrative embodiment shown, optical properties have been plotted whose value in the cervical area 16, that is to say principally for the cervical compound, and in the incisal area 18, that is to say principally for the incisal compound, is the same. It will, be appreciated that this is a simplified representation and that in practice, at least for "some optical properties, it relates to standardized values. For example, the color saturation in the cervical area 16 is typically much greater than in the incisal area 18. For clarity, the representation according to FIG. 3 has to this extent been based on standardized values, it being understood that standardization is not required when using a combination with other optical properties such as reflectance.

It will be seen from FIG. 4 that the optical properties across the entire transition area 20 change with the same variation gradient. The transition area 20 is delimited by the crossover areas 22 and 24, which are adjoined respectively by the cervical area 16, on the one hand, and by the incisal area 18, on the other hand.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A block made of ceramic compounds for the dental sector comprising at least a first ceramic compound with predetermined optical properties, whereas the optical properties comprise at least a first translucency, a first brightness, a first reflectance and a first color and at least a second ceramic compound with a second translucency, a second brightness, a second reflectance and a second color, and the at least two ceramic compounds are mixed in changing mixing ratios, wherein a transition area (20), between the first ceramic compound (15) and the second ceramic compound (17), is composed of mixtures of the at least two ceramic compounds (15, 17) and set with such a gradient that the variation gradient of the resulting optical properties is substantially constant in the transition area.

2. The block as claimed in claim 1, wherein, in addition to the transition area at least one area with substantially constant optical properties is provided.

3. The block as claimed in claim 2, wherein, between the area with constant optical properties in which the variation gradient=0 and the transition area with a substantially constant variation gradient, a crossover area (22, 24) is provided in which the gradient changes from zero to the non zero value of the variation gradient.

4. The block as claimed in claim 1, wherein the block (10) has substantially a cuboid shape, with the length and width each being smaller than the height.

5. The block as claimed in claim 1, wherein the block (10) is in a cuboid shape, with the length or width being greater than the height.

6. The block as claimed in claim 1, wherein the block (10) has substantially a cuboid shape, the midpoint of its height being formed by the transition area.

7. The block as claimed in claim 1, wherein the block (10) is formed from a granulate of which at least 95% by weight has a $d_{50}$ particle size in the range from 0.1 micrometer to 2 millimeters, at least 90% by weight in the range from 1 micrometer to 700 micrometers, and at least 85% by weight in the range from 50 to 400 micrometers.

8. The block as claimed in claim 1, wherein the block (10) is constructed from ceramic compounds (15, 17) whose primary particle size is smaller than 10 micrometers and greater than 10 nanometers.

9. The block as claimed in claim 1, wherein the block (10) is produced in a mold which is acted upon by at least one press ram in order to generate substantially a cuboid shape or tablet shape.

10. The block as claimed in claim 9, wherein the mold is acted upon by two press rams lying opposite one another.

11. The block as claimed in claim 1, wherein the block (10) is produced from a metered layering of ceramic compounds (15, 17).

12. The block as claimed in claim 1, wherein, the first color is according to a color key used in the dental industry.

13. A block made of ceramic compounds for the dental sector with at least a first ceramic compound (15) with predetermined optical properties, and with at least a second ceramic compound (17) with predetermined optical properties, and the at least two ceramic compounds are mixed in changing mixing ratios, wherein, in a transition area between the first ceramic compound (15) and the second ceramic compound (17), the variation profile of the mixing ratio at an inner location of the block (10) is different than at the edge of the block (10), relative to a sectional plane of the block (10) parallel to its base.

14. The block as claimed in claim 13, wherein the locations of identical mixing ratio between the two ceramic compounds (15, 17) lie on a surface that differs from a plane.

15. The block as claimed in claim 14, wherein the locations of identical mixing ratio between the two ceramic compounds (15, 17) lie on a surface that is curved.

16. The block as claimed in claim 13, wherein the surface is substantially a cone surface, the cone angle of which is greater than zero and smaller than approximately 30°.

17. The block as claimed in claim 16, wherein the surface is substantially a cone surface, the cone angle of which is greater than 0.5°.

18. The block according to claim 13, wherein, in the transition area between the first ceramic compound (15) and the second ceramic compound (17), the variation profile of the mixing ratio in the center is different than at the edge of the block (10), relative to a sectional plane of the block (10) parallel to its base.

19. A block made of ceramic compounds for the dental sector with at least a first ceramic compound (15) with predetermined physical properties, whereas the first physical properties comprise at least a first flexural strength, a first compression strength, a first abrasion resistance, a first hardness and a first modulus of elasticity, and with at least a second ceramic compound (17) with second predetermined physical properties, whereas the second physical properties comprise at least a second flexural strength, a second compression strength, a second abrasion resistance, a second hardness and a second modulus of elasticity, and the at least two ceramic compounds are mixed in changing mixing ratios, wherein, in a transition area between the first ceramic compound (15) and the second ceramic compound (17), this is constructed from a mix of at least the two ceramic compounds (15, 17), and the mixing ratio of these at least two ceramic compounds (15, 17) is set with such a gradient that the variation gradient of the resulting mechanical properties each measured on the block, is substantially constant in the transition area whereas the resulting mechanical properties comprise the flexural strength, the compression strength, the hardness and abrasion resistance.

20. The block as claimed in claim 19, made of at least one ceramic compound with predetermined first optical and mechanical properties, a first translucency, a first brightness, a first reflectance, a first color, a first flexural strength, a first compression strength, a first hardness and a first abrasion resistance, measured on the thermally treated block, and with at least a second ceramic compound with a second translucency, a second brightness, a second reflectance, a second color, a second flexural strength, a second compression strength, a second hardness and a second abrasion resistance, wherein, in a transition area between the first ceramic compound (15) and the second ceramic compound (17), points with identical optical properties on the outside lie in a different plane than inside the block (10).

* * * * *